United States Patent [19]

Matukas

[11] Patent Number: 4,645,488
[45] Date of Patent: Feb. 24, 1987

[54] SYRINGE FOR EXTRUSION OF WETTED, PARTICULATE MATERIAL

[75] Inventor: Victor J. Matukas, Mountain Brook, Ala.

[73] Assignee: Board of Trustees of the University of Alabama, Birmingham, Ala.

[21] Appl. No.: 556,725

[22] Filed: Nov. 30, 1983

Related U.S. Application Data

[63] Continuation-in-part of Ser. No. 407,424, Aug. 12, 1982, abandoned.

[30] Foreign Application Priority Data

Jul. 27, 1983 [NZ] New Zealand .................. 205033

[51] Int. Cl.⁴ ............................................. A61M 31/00
[52] U.S. Cl. ..................................... 604/59; 604/218
[58] Field of Search ................. 604/59, 55, 60, 48, 604/904, 57, 49, 54, 287, 11–18, 230, 218, 222

[56] References Cited

U.S. PATENT DOCUMENTS

| | | | |
|---|---|---|---|
| 2,754,822 | 6/1956 | Emelock | 604/218 |
| 3,424,158 | 1/1969 | Silver | 604/59 |
| 3,633,585 | 1/1972 | McDonald, Jr. | 604/280 X |
| 3,753,437 | 8/1973 | Hood et al. | 604/14 |
| 3,828,767 | 8/1974 | Spiroff | 604/280 X |
| 3,918,452 | 11/1975 | Cornfeld | 604/55 |
| 3,934,584 | 1/1976 | Corio | 604/59 |
| 3,960,153 | 6/1976 | Carey et al. | 604/164 |
| 4,046,145 | 9/1977 | Choksi et al. | |
| 4,060,082 | 11/1977 | Lindberg et al. | |
| 4,280,500 | 7/1981 | Ono | 604/280 |
| 4,318,402 | 3/1982 | Vaillancourt | 604/280 |
| 4,464,176 | 8/1984 | Wijayarathna | 604/164 |
| 4,493,696 | 1/1985 | Uldall | 604/43 |
| 4,540,404 | 9/1985 | Wolvek | 604/96 |
| 4,545,390 | 10/1985 | Leary | 604/96 |
| 4,551,135 | 11/1985 | Gorman | 604/218 |
| 4,571,240 | 2/1986 | Samson et al. | 604/96 |
| 4,573,470 | 3/1986 | Samson et al. | 128/772 |

FOREIGN PATENT DOCUMENTS 0006545  6/1979  European Pat. Off. .............. 604/82

OTHER PUBLICATIONS

USCI Catalogue 1974/5070107.

*Primary Examiner*—John D. Yasko
*Attorney, Agent, or Firm*—William G. Webb; B. Woodrow Wyatt; Paul E. Dupont

[57] ABSTRACT

The invention relates to a syringe for extrusion of a semi-plastic, particulate mass comprising a barrel of flexible material having one or more longitudinal slits therein and provided at its upper end with a piston with means for making positive engagement with a plunger rod, the barrel being optionally fitted with a closure plug.

34 Claims, 3 Drawing Figures

SYRINGE FOR EXTRUSION OF WETTED, PARTICULATE MATERIAL

CROSS REFERENCE TO RELATED APPLICATIONS

This is a continuation-in-part of my prior co-pending application Ser. No. 407,424, filed Aug. 12, 1982 now abandoned.

BACKGROUND OF THE INVENTION (a) Field of the Invention

This invention relates to a syringe useful in extruding a semi-plastic, particulate mass therefrom.

(b) Information Disclosure Statement

The use of two component mixing syringes for dissolving a solid medicament in a liquid diluent prior to injection of the solution is well known in medical practice. An example of such syringes is illustrated by Lindberg et al. U.S. Pat. No. 4,060,082, which describes a syringe combination comprising a mixer/dispenser syringe, usually containing a solid medicament, which is connected via a collapsible connecting sleeve to a carrier syringe, usually containing a liquid diluent used to dissolve the medicament in the mixer/dispenser section. When it is desired to use the syringe, the two syringe sections are telescoped together thus forcing a fill needle positioned between the two syringe sections to make a communicating connection between the mixer/dispenser and the carrier syringe sections. The liquid contents of the carrier section can then be ejected through the fill needle into the mixer/dispenser section. After the solid medicament has dissolved, a hypodermic needle is attached to the exit end of the mixer/dispenser section, a plunger is attached to a rubber piston closing the other end, and the liquid contents can then be ejected.

There are various means for making connection between two sections of a two component mixing syringe, the collapsible sleeve and filling needle described in the above-noted Lindberg et al. patent being one such means. Another means of achieving such inter-connection is illustrated in Choksi et al. U.S. Pat. No. 4,046,145 which describes a Luer lock/Luer joint two-part unit.

However, syringes for dispensing liquids are difficult to use in the extrusion of semi-plastic, particulate masses, and may in some cases be inoperative for such purpose. While the prior art is thus instructive on the problem of mixing two components and dispensing a resulting solution in liquid form, so far as is known, the art is silent on the problem of mixing two or more components within a syringe barrel, so as to form a semi-plastic, particulate mass, for extrusion thereof.

It has been found that particulate matter, such as particulate ceramic material used in dental restorative procedures, even when wetted, tends to jam in the barrel when extruded from conventional syringes, perhaps due to frictional resistance between the sharp edges of the particles and the syringe barrel wall. I have discovered that the problem can be overcome by equipping the syringe barrel, which is advantageously fabricated of a flexible plastic material, with one or more longitudinal slits in the barrel. The provision of such slits has the effect of providing sufficient relief from the frictional resistance to permit unobstructed extrusion of particulate material from the barrel.

BRIEF SUMMARY OF THE INVENTION

The present invention therefore is directed, in one aspect, to a dispensing syringe useful for extruding a semi-plastic, particulate mass therefrom which comprises (A) a barrel of flexible plastic material having one or more longitudinal slits therein and which is provided at its upper end with (B) a piston having means for making positive engagement with (C) a plunger rod, the barrel being optionally fitted with (D) a closure plug. The syringe may, if desired, be pre-loaded with a particulate component which, on admixture with a liquid component, would produce a semi-plastic, extrudable mass. In a preferred embodiment, the dispensing syringe of the invention is adapted for use in dental restorative surgery in alveolar ridge augmentation procedures.

In a second aspect, the invention relates to a method of using the said syringe in such dental restorative processes.

BRIEF DESCRIPTION OF THE DRAWINGS

In order to fully describe the invention herein and the manner of using it, it will be necessary to use certain portions of a syringe unit as points of reference to illustrate relative movements of the parts of the syringe. Therefore, throughout this specification and in the appended claims, the terms "lower" and "downwards" are intended to refer to the exit end of the syringe and its various associated parts as assembled or oriented in the syringe for extruding use, and the terms "upper" and "upward" are intended to refer to the opposite or head end of the same.

The invention is described hereinbelow with reference to the accompanying drawings wherein.

DETAILED DESCRIPTION OF THE INVENTION

The invention will now be described in detail with reference to the foregoing figures where like numerals are used to designate like parts.

Figure 1:
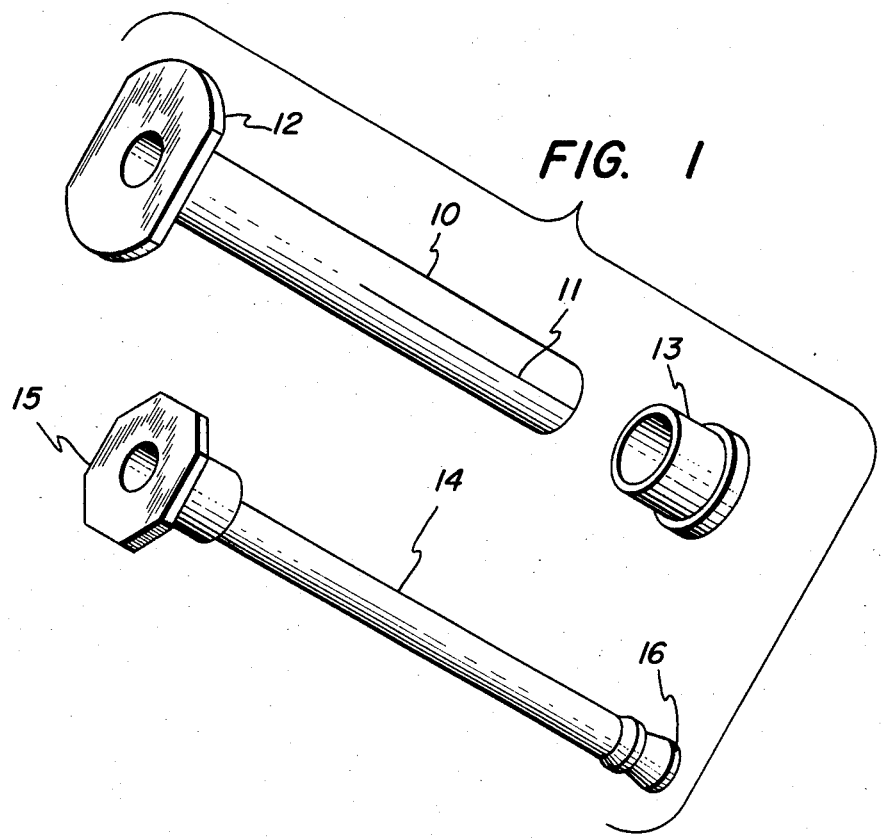
FIG. 1 is a perspective view of the barrel, closure plug, plunger and piston units which comprise the principal elements of the syringe.

FIG. 1 shows the various principal elements of the syringe including the syringe barrel unit 10 having a longitudinal slit 11 and equipped with finger grip head 12. The barrel is fitted with a closure plug 13 which fits over the lower end of the barrel to prevent a particulate component of an extrudable mass from falling out of the end of the barrel. The syringe is also equipped with a plunger rod unit 14 having a thumb plate 15 at its upper end. The lower end of the plunger rod is equipped with a piston 16 which is slidable within the bore of the syringe barrel 10. The plunger rod 14 and the piston 16 are preferably non-unitary parts, made of different materials and joined together by any means effective for making positive interconnection, such as by a ball and socket connection in which a spheroid or elongate spheroid shape is used on the lower end of the plunger rod to mate with a cavity of corresponding shape molded into the piston.

Figure 2:
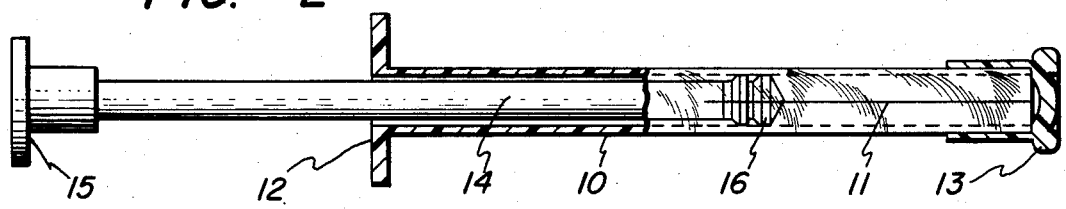
FIG. 2 is a longitudinal view in partial cross section of the syringe as assembled prior to use.
Figure 3:
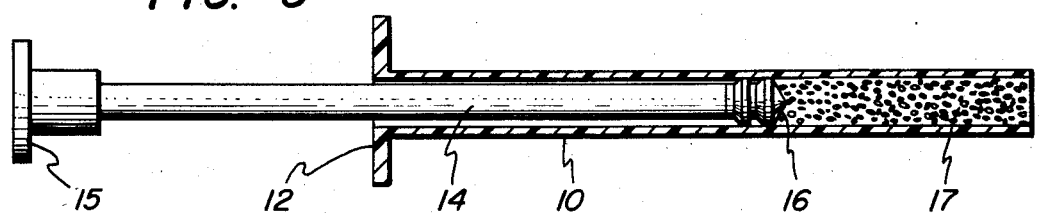
FIG. 3 is a longitudinal view in partial cross section of the assembled syringe in use.

FIG. 2 shows the principal elements of the syringe as they would appear when assembled prior to loading with any component of an extrudable mass and prior to use, and FIG. 3 shows the principal elements of the syringe containing an extrudable mass 17 as the syringe would appear in use.

The syringe provided by the invention would be particularly useful in the field of dental surgery and especially in alveolar ridge augmentation procedures in edentulous patients. In such patients, over a period of time the alveolar ridge undergoes gradual bone resorption with consequent diminution in height of the alveolar ridge. This process in turn produces a condition whereby dentures must be remolded and fitted to a continuously changing gum shape. The problem can be alleviated by restructuring the alveolar ridge with a material that is capable of bonding to osseous tissue, is non-resorbable and provides a matrix for new bone growth. Materials which have been found useful for this purpose are certain ceramic materials, including especially hydroxylapatite. The process for preparing hydroxylapatite and the use of this material in dental restorative processes are disclosed in U.S. Pat. No. 4,097,935.

In using the syringe of the present invention in dental restorative procedures as described above, the barrel 10 of the syringe would be filled with the powdered or granulated ceramic material, e.g. hydroxylapatite.

The slit 11 in the barrel is formed either by merely slitting the barrel wall after fabrication of the latter or by molding the slit into the barrel at the time of fabrication. The purpose of the slit is to provide a means for slight circumferential expansion of the barrel along its operative length as the piston moves therealong in order to thereby slightly relieve the frictional resistance between the particulate material and the barrel wall. This construction permits unobstructed extrusion of the particulate material while still preserving the general cross sectional form of the extruded mass. In order to achieve this objective, therefore, the length of the slit preferably corresponds approximately to the length of the extrudable mass as it would appear when packed into the syringe barrel for use. That is, the slit extends up to, but preferably not beyond, the piston as it would be positioned in the barrel prior to use.

In preparing the syringe for use, the dental surgeon would insert the tip of the syringe in saline, distilled water or other suitable delivery fluid, and, by withdrawing the plunger rod, draw the liquid up into the barrel of the syringe through the slit 11, thus producing a wetted, extrudable mass of the granular ceramic material. Alternatively, the syringe barrel containing the particulate material can be held upright while the delivery fluid is added to the open end of the syringe either by pouring from another container or by injection with a second syringe or fluid dropper. Another fluid suitable for use in dental restorative purposes would be the patient's own blood, and the latter method of admixing fluid with particulate matter is particularly adaptable when blood is used for such purpose. The use of the blood in dental restorative processes is particularly advantageous, because, if the blood/ceramic mixture is allowed to stand for a short time before use, the blood begins to coagulate to form a semi-plastic coagulum which can be readily extruded from the syringe.

Prior to preparation of the ceramic/delivery fluid, for example a ceramic/saline or ceramic/blood mixture as described above, the surgeon would intraorally prepare a mucoperiosteal tunnel through a vertical incision on the lateral aspect of the patient's jaw. The closure plug 13 would then be removed from the syringe, and the barrel thereof inserted through the incision into the tunnel formed adjacent the alveolar ridge. By slowly withdrawing the syringe barrel from the tunnel while extruding the syringe contents by downward pressure on the plunger, the extrudable, wetted ceramic mass would be deposited into the prepared mucoperiosteal tunnel adjacent the alveolar ridge. Ultimately the ceramic mass will bond to the cortical bone thereby augmenting the alveolar ridge.

When used in alveolar ridge augmentation procedures as described above, the syringe barrel 11 can advantageously be supplied with appropriate indicia as an aid in determining the amount and the rate of extrusion of the plasticized material from the barrel.

The syringe of the invention is suitably made of an appropriate plastic material which, when used in dental restorative processes, can be sterilized by autoclaving, gas or irradiation. Thus the barrel and finger grip can be made of polyethylene or polypropylene, while the plunger rod is suitably made of styrene or nylon. The closure plug and the piston can be made of either the same or different flexible material, such as a natural or synthetic elastomer or rubber, for example a vinyl or butyl rubber, including brominated or chlorinated butyl rubbers or neoprene.

It will be understood that, although preferred embodiments have been described above in order to better illustrate the invention, alternative materials, forms and the like can be substituted for such aspects specifically described herein without either departing from the spirit of the invention or in any way adversely affecting the operability of the same.

For example, the means for making positive interconnection between the plunger rod and the piston has been described herein, for purposes of illustration, in terms of a spheroid or elongate spheroid shape on the end of the plunger rod with a cavity of corresponding shape molded into the piston. However, any of various means well known in the art for making such inter-connection that would be operative for the stated purpose are considered to be within the ambit of the invention. Such alternative means of effecting inter-connection include, for example, a bayonet, or push-and-turn, connection, or a screw-threaded tip and socket on the plunger and piston, respectively. These, and other similarly effective inter-connecting means, are thus the full equivalents of the ball and socket inter-connection specifically described herein.

Having thus described the invention and the advantages thereof, it is considered that the invention is to be broadly construed and limited only by the character of the following claims.

I claim:

1. A dental restorative dispensing syringe for extruding a wetted particulate mass therefrom which comprises: (A) a barrel of flexible plastic material having at least one longitudinal slit therein at its open end in combination with (B) a piston slidable within the bore of said barrel providing a seal between said piston and the inside wall of the barrel along its entire length and having means for making positive engagement with (C) a plunger rod, the length of said slit being approximately equal to the length of the wetted particulate mass to be extruded therefrom and being operative to allow said barrel to expand under the influence of said wetted particulate mass when said piston is extruding said mass, thereby reducing barrel resistance.

2. A dispensing syringe according to claim 1 wherein said barrel has one longitudinal slit therein.

3. A dispensing syringe according to claim 1 which is fitted with a closure plug at its lower end.

4. A dispensing syringe according to claim 1 which is pre-loaded with a particulate material.

5. A dispensing syringe according to claim 1 wherein said particulate material is hydroxylapatite.

6. A dispensing syringe according to claim 2 wherein said particulate material is hydroxylapatite.

7. A dispensing syringe according to claim 3 wherein said particulate material is hydroxylapatite.

8. A dispensing syringe according to claim 4 wherein said particulate material is hydroxylapatite.

9. An alveolar ridge augmentation device comprising: (a) a barrel member of flexible material defining a bore, said barrel member having an open end; (b) a wetted mass of particulate ridge augmentation material within said bore; (c) means operatively coupled with said barrel member for expressing said wetted mass from said bore through said open end; (d) said barrel member having at least one expansion slit extending longitudinally from said open end, the length of said slit being approximately equal to the length of the wetted particulate mass to be expressed therefrom and being operative to allow said barrel member to expand under the influence of said wetted mass when said means is expressing said wetted mass, thereby reducing barrel resistance to said wetted mass.

10. The device according to claim 9 wherein said barrel member is flexible plastic material.

11. The device according to claim 9 wherein said barrel member is circular in cross-section.

12. The device according to claim 9 wherein said barrel member has one slit therein.

13. The device according to claim 10 wherein said barrel member has one slit therein.

14. The device according to claims 11 wherein said barrel member has one slit therein.

15. The device according to claim 9 wherein said particulate mass is ceramic hydroxylapatite.

16. The device according to claim 10 wherein said particulate mass is ceramic hydroxylapatite.

17. The device according to claim 11 wherein said particulate mass is ceramic hydroxylapatite.

18. A method of delivering a wetted mass of particulate dental restorative material with a dispensing syringe in alveolar ridge augmentation procedures in a patient requiring such treatment, said dispensing syringe comprising: (A) a barrel for containing said material, said barrel being of flexible material fitted with a closure plug at its lower end and having at least one longitudinal slit therein extending from its lower end towards its upper end in combination with (B) a piston having means for making positive engagement with (C) a plunger rod, the length of said slit being approximately equal to the length of the wetted particulate mass to be delivered therefrom and being operative to allow said barrel to expand under the influence of said wetted mass when said piston is extruding said mass thereby reducing barrel resistance, which method comprises: (1) producing a wetted mass of the particulate material by addition of delivery fluid to said particulate material, (2) inserting the syringe barrel into a mucoperiosteal tunnel on the lateral aspect of the patient's jaw after removal of said closure plug and (3) extruding said wetted, particulate material into said mucoperiosteal tunnel while withdrawing said syringe barrel from said tunnel.

19. A method according to claim 18 wherein said delivery fluid is saline.

20. A method according to claim 18 wherein said delivery fluid is distilled water.

21. A method according to claim 18 wherein said delivery fluid is blood.

22. A method according to claim 18 wherein said barrel is flexible plastic material.

23. A method according to claim 18 wherein said particulate material is hydroxylapatite.

24. A method according to claim 19 wherein said particulate material is hydroxylapatite.

25. A method according to claim 20 wherein said particulate material is hydroxylapatite.

26. A method according to claim 21 wherein said particulate material is hydroxylapatite.

27. A method according to claim 22 wherein said particulate material is hydroxylapatite.

28. A method for augmenting the alveolar ridge in an edentulous patient comprising the steps of: (1) providing a charge of particulate dental restorative material; (2) providing a delivery fluid; (3) mixing said delivery fluid with said charge to form a wetted extrudable mass; (4) forming a mucoperiosteal tunnel on the lateral aspect of the patient's jaw; (5) depositing said wetted mass in said tunnel by extruding it from a barrel having at least one expansion slit extending longitudinally from its open end, the length of said slit being approximately equal to the length of the wetted mass to be extruded therefrom and being operative to allow said barrel member to expand under the influence of said wetted mass as it is extruded, thereby reducing barrel resistance to said wetted mass.

29. A method according to claim 28 further comprising the step of withdrawing the barrel from said tunnel while extruding said mass.

30. A method according to claim 28 wherein said particulate material is hydroxylapatite, whitlockite or mixtures thereof.

31. A method according to claim 29 wherein said particulate material is hydroxylapatite, whitlockite or mixtures thereof.

32. A method according to claim 26 wherein the particulate material is wetted with saline.

33. A method according to claim 26 wherein the particulate material is wetted with the patient's blood.

34. A method of alveolar ridge augmentation in a patient requiring such treatment by use of a dispensing syringe for dispensing a wetted particulate material, said syringe comprising (a) a barrel of flexible material defining a bore, said barrel member having an open end; (b) a mass of particulate ridge augmentation material within said bore; (c) means operatively coupled with said barrel member for expressing said particulate material from said bore through said open end; (d) said barrel member having at least one expansion slit extending longitudinally from said open end, the length of said slit being approximately equal to the length of the wetted particulate material to be expressed therefrom and being operative to allow said barrel member to expand under the influence of said wetted material when said means is expressing said wetted material, thereby reducing barrel resistance to said wetted material, which method comprises (1) drawing saline or distilled water into the syringe by withdrawal of said plunger rod while immersing the tip of the same in either saline or distilled water or by addition of the patient's blood to the syringe to thereby produce a wetted mass of the particulate material, (2) inserting the syringe barrel into a mucoperiosteal tunnel on the lateral aspect of the patient's jaw and (3) extruding said wetted, particulate material into said mucoperiosteal tunnel while withdrawing said syringe from said tunnel.

* * * * *